(12) United States Patent
Dijkstra et al.

(10) Patent No.: US 11,280,705 B2
(45) Date of Patent: Mar. 22, 2022

(54) SYSTEM AND METHOD FOR MEASURING A CONCENTRATION OF A POLLUTANT WITHIN A GAS (71) Applicant: KONINKLIJKE PHILIPS N. V., Eindhoven (NL)

(72) Inventors: Jacob Dijkstra, Zwaagwesteinde (NL); Timothy Van Der Graaf, Groningen (NL); Einte Holwerda, Stadskanaal (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 200 days.

(21) Appl. No.: 16/471,184

(22) PCT Filed: Dec. 25, 2017

(86) PCT No.: PCT/EP2017/084577
§ 371 (c)(1),
(2) Date: Jun. 19, 2019

(87) PCT Pub. No.: WO2018/115531
PCT Pub. Date: Jun. 28, 2018

(65) Prior Publication Data
US 2020/0025399 A1 Jan. 23, 2020

(30) Foreign Application Priority Data

Dec. 23, 2016 (EP) ..................................... 16206557

(51) Int. Cl.
G01N 1/22 (2006.01)
F24F 11/39 (2018.01)
(Continued)

(52) U.S. Cl.
CPC ............. *G01N 1/2205* (2013.01); *F24F 8/10* (2021.01); *F24F 11/39* (2018.01); *G01N 1/2273* (2013.01);
(Continued)

(58) Field of Classification Search
CPC .... G01N 1/2205; G01N 1/2273; G01N 15/06; G01N 33/0009; G01N 33/0011;
(Continued)

(56) References Cited

U.S. PATENT DOCUMENTS 6,615,842 B1 9/2003 Cerami
7,835,005 B2 11/2010 Appel
(Continued)

FOREIGN PATENT DOCUMENTS

CN 101368921 A 2/2009
CN 202330348 U 7/2012
(Continued)

OTHER PUBLICATIONS

PCT/EP2017/084577 International Search Report.

*Primary Examiner* — Benjamin R Schmitt (57) ABSTRACT

An air purification system is provided which includes measurement of a concentration of a target pollutant within the air. A gas sensor is used for sensing a concentration of the pollutant (although it will detect other pollutants as well due to cross-sensitivity). A filter is provided which selectively removes the target pollutant while having a significantly smaller effect in reducing other pollutants to which the sensor is cross-sensitive. A gas sensor response is obtained before filtering, a gas sensor response after filtering, and the sensitivity characteristics of the gas sensor to the pollutant are processed, thereby to determine a gas concentration of the pollutant in the air before filtering. In this way, the concentration measurement is better than a direct measure-
(Continued)

ment with the gas sensor as a result of a low selectivity of the gas sensor.

14 Claims, 3 Drawing Sheets

(51) Int. Cl.
| | |
|---|---|
| *G01N 15/06* | (2006.01) |
| *G01N 33/00* | (2006.01) |
| *F24F 8/10* | (2021.01) |
| *F24F 110/50* | (2018.01) |
| *F24F 110/66* | (2018.01) |
| *G01N 15/00* | (2006.01) |
| *F24F 8/99* | (2021.01) |

(52) U.S. Cl.
CPC .......... *G01N 15/06* (2013.01); *G01N 33/0011* (2013.01); *G01N 33/0047* (2013.01); *F24F 8/99* (2021.01); *F24F 2110/50* (2018.01); *F24F 2110/66* (2018.01); *G01N 2015/0046* (2013.01); *G01N 2015/0662* (2013.01)

(58) Field of Classification Search
CPC ........... G01N 33/0036; G01N 33/0047; G01N 2015/0046; G01N 2015/0662; G01N 2015/0065; F24F 11/39; F24F 8/10; F24F 8/99; F24F 2110/50; F24F 2110/66; F24F 11/30

See application file for complete search history.

(56) References Cited

U.S. PATENT DOCUMENTS

| | | | |
|---|---|---|---|
| 2006/0234621 A1* | 10/2006 | Desrochers | ............ F24F 3/044 |
| | | | 454/239 |
| 2008/0034842 A1 | 2/2008 | Lee | |
| 2009/0126454 A1 | 5/2009 | Pratt | |
| 2014/0174154 A1* | 6/2014 | Marra | ................ G01N 27/4045 |
| | | | 73/31.01 |

FOREIGN PATENT DOCUMENTS

| | | | |
|---|---|---|---|
| CN | 202421111 U | 9/2012 | |
| CN | 203443606 U | 2/2014 | |
| WO | 97045189 A1 | 12/1997 | |
| WO | WO-2010025600 A1 * | 3/2010 | ......... G01N 33/0009 |
| WO | 2012069963 A1 | 5/2012 | |
| WO | 2013008170 A2 | 1/2013 | |

* cited by examiner

SYSTEM AND METHOD FOR MEASURING A CONCENTRATION OF A POLLUTANT WITHIN A GAS

This application is the U.S. National Phase application under 35 U.S.C. § 371 of International Application No. PCT/EP2017/084577, filed on Dec. 25, 2017 and International Application No. 16206557.7, filed Dec. 23, 2016. These applications are hereby incorporated by reference herein.

FIELD OF THE INVENTION

This invention relates to sensing pollutant levels in a gas, such as air.

BACKGROUND OF THE INVENTION

Indoor air pollution presents a significant health hazard in many urbanized areas across the world. Air pollution sources are encountered both outdoors (e.g. from motor vehicles and industry) and indoors (from cooking, smoking, candle burning, incense burning, outgassing building/decoration materials, use of outgassing waxes, paints, polishes etc.). The pollution level indoors is often higher than outdoors, especially for volatile organic compounds. At the same time, many people reside most of their time indoors and may thus be almost continuously exposed to unhealthy levels of air pollution.

One method to improve the indoor air cleanliness is by installing an air cleaner indoors which is capable of continuously recirculating the indoor air through a cleaning unit comprising one or more air filters, or using adsorption, chemisorption, conversion or decomposition. Examples are activated carbon filters, porous media impregnated with chemicals, photocatalytic units, plasma-based components or biological based purification components.

Another method to improve the indoor air cleanliness is by applying continuous ventilation with filtered outdoor air. In the latter case, the air filter(s) are usually comprised in a heating, ventilation and air conditioning (HVAC) system capable of temperature adjustment, ventilation, and of cleaning the ventilation air drawn from outdoors by passing it first through one or more air filters before releasing it indoors. Ventilation with cleaned outdoor air displaces polluted indoor air and dilutes the pollution level therein.

For removing polluting gases from air, use is of often made of activated carbon filters which are capable of adsorbing/removing/decomposing many volatile organic hydrocarbon gases (VOCs) and several inorganic gases (NO2, O3, SO2) from air. The activated carbon material is usually present as powder, granules or pellets that are contained in an air-permeable filter frame structure.

Indoor air pollution with formaldehyde gas is a particular problem affecting the health and well-being of many people. Formaldehyde is continuously emitted from indoor sources such as building materials, decoration material, and furniture. Its indoor concentration can increase to well above the clean air guideline concentrations for formaldehyde (as an example, a Chinese guideline defines a maximum acceptable formaldehyde exposure of 0.10 mg/m$^3$—other countries can have other guidelines) when the room is poorly ventilated. High ventilation conditions achieved by opening windows and doors are not always feasible due to outdoor weather conditions, an uncomfortable outdoor temperature, and/or safety considerations.

There is an increasing desire to be able to measure pollutant concentrations in the home. Determining the pollutant concentration in homes is difficult. For example, air extraction over gas absorbing tubes via a vacuum pump may be used, followed by gas chromatography analysis of the tubes to measure the different concentrations. Such an analysis typically takes around 4 hours for the extraction and the gas chromatography analysis is performed at a laboratory and takes approximately a day. This is clearly a costly and time consuming process. It also gives only one measurement and no indication of the changes in gas concentration over time. The measurement can only be done by experts with expensive equipment.

The accuracy of current gas sensors is limited due to cross-sensitivity and low reaction speed. Cross-sensitivity is common for electrochemical based sensors.

For example, the table below shows sensitivity (in change in output voltage V to 1 ppm of various gases) of a known electrochemical based formaldehyde sensor of the company Membrapor AG (Trade Mark).

| gas | Membrapor responsivity R ($\Delta$V/ppm) |
| --- | --- |
| formaldehyde | 0.36 |
| acetaldehyde | ~0.01 |
| propanal | 0.07 |
| hexanal | 0.07 |
| methanol | 0.1 |
| ethanol | 0.19 |
| iso-propanol | 0.12 |
| 1-butanol | 0.2 |
| acetone | 0.0005 |
| acetic acid | 0 |
| toluene | 0 |

The above table indicates that this specific sensor responds to alcohols and higher aldehydes. This cross-sensitivity can give a strong contribution to the overall sensor signal as alcohols can be emitted in homes by cleaning agents and air fresheners, personal hygiene products such as shaving lotions or deodorizers as well as from alcoholic drinks.

An extensive study in 50 homes in Canada measured VOC levels as present during normal household activities. The average measured ethanol levels exceeded the formaldehyde concentrations with a factor of 10 times or more. Table 1 shows that in such atmospheres, the cross-sensitivity response exceeds the signal due to formaldehyde gas.

Thus, because the sensor is responsive to a variety of gases, it has a limited selectivity.

There are other gases giving rise to cross-sensitivity issues, for example hydrogen gives rise to a cross-sensitivity of 1 to 3% and CO gives rise to a cross-sensitivity of 10 to 18%.

WO 2013/008170 discloses a gas sensing apparatus in which there is a filtered gas channel and an unfiltered gas channel, with gas sensor measurements sequentially from each channel. The measurements are combined to provide a concentration reading. This solution can be influenced by rapid changes in VOC levels because of human activities during the differential gas level measurement. In addition, a more simple solution with less components would be preferred to improve manufacturability and reduce cost.

There is therefore a need for a low cost and time efficient way to provide accurate readings of a gas concentration of a pollutant, in particular for an air purifier which is installed to remove a target VOC pollutant.

SUMMARY OF THE INVENTION

The invention is defined by the claims.

According to examples in accordance with an aspect of the invention, there is provided an air purification system, comprising:
- a filter for selectively filtering a pollutant from the air;
- a gas sensor for sensing a concentration of the pollutant in the air;
- a controller, which is adapted to process a first unfiltered gas sensor response, a second gas sensor response when the concentration of the pollutant in the air has been stabilized by filtering, and the sensitivity characteristics of the gas sensor to the pollutant, thereby to determine a gas concentration of the pollutant in the air before filtering.

This system obtains a concentration measurement by processing the drop in gas sensor response measured by a gas sensor with known dose response curve to the pollutant, when the pollutant is filtered out by a selective filter. The gas sensor response is measured in the presence of the pollutant (e.g. before filtering) and after filtering once the pollutant levels have stabilized to a lower level. This may be several minutes or hours after initially turning on the device.

The air purification system may be turned on automatically, for example in the absence of a user. The system can thus report to the user that it was automatically turned on, and report the pollutant levels before and after the filtering process. This provides reassurance about the concentration of the target pollutant in the air. The concentration of components emitted by decoration and which can pose a health risk, like formaldehyde, decrease as a function of time but also depend on temperature and humidity. Regular detection of such a component demonstrates to the inhabitant if the background concentration of the component that poses a health risk has reduced and possibly even reached acceptable values.

The concentration within the ambient air changes during the sensing operation because the pollutant is removed. Identical sensing operations may be carried out before and after the pollution filtering using a simple single sensor. The sensing may also be carried out using normal convection.

The filter preferably has greater selectivity to the pollutant than the gas sensor. In this way, the cross-sensitivity of the gas sensor can be tolerated, because the more selective filter ensures that a change in concentration only of the pollutant is responsible for the change in gas sensor reading.

The pollutant is for example formaldehyde. Highly selective formaldehyde filters are known as well as formaldehyde sensors, although the sensors are also responsive to other gases.

The controller may be adapted to obtain the first unfiltered gas sensor response when a stable response of the gas sensor reading is obtained. Thus, both sensor readings are obtained when stable sensor outputs have been monitored, indicating that the environment is stable without human influence before filtering, and that the filtering has reached a steady state.

The controller may be adapted to operate the device after a stable response of the gas sensor is obtained. This provides automated filter operation when stable high pollutant levels are detected, i.e. not influenced by users. This may be in the absence of users from the confined space, so that automatic control of the device is provided.

The controller may be adapted to obtain the first unfiltered gas sensor response before the filtering and to obtain the second gas sensor response after the filtering. In this way, as soon as the filtering is complete, a concentration measurement is available.

Examples in accordance with another aspect of the invention provide an air purification method comprising:
- selectively filtering a target pollutant;
- monitoring a gas sensor response using a gas sensor until the gas sensor response has stabilized;
- obtaining a second gas sensor response after the filtering;
- processing a first unfiltered gas sensor response relating to the unfiltered pollutant concentration, the second gas sensor response, and the sensitivity characteristics of the gas sensor to the target pollutant, thereby to determine a concentration of the target pollutant in the air before filtering.

This method provides air purification as well as an accurate report on the concentration levels of the pollutant being filtered, before the filtering operation. It informs the user if the target pollutant still can pose a health risk in the confined space or not. The method may use a single sensor.

A gas sensor response may be sensed a plurality of times before selectively filtering and the first unfiltered gas sensor response may then be obtained when a stable response of the gas sensor is obtained. This ensures the unfiltered gas sensor reading is not influenced by dynamic factors such as human activity and instead represents a general ambient level of pollution, which is of most concern for users.

The filter may be operated after a stable response of the gas sensor is obtained. This provides automated filter operation when needed.

The first unfiltered gas sensor response may be obtained before the filtering and the second gas sensor response may be obtained after the filtering.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides an air purification system which includes measurement of a concentration of a target pollutant within the air. A gas sensor is used to determine a concentration of the target pollutant (although it will respond to other pollutants as well due to cross-sensitivity). A filter is provided which is selectively filtering the target pollutant. while having a significantly smaller effect in reducing other pollutants to which the sensor is cross-sensitive. Thus, the filter has no, or no significant effect in reducing those other pollutants. A gas sensor response is obtained before filtering, a gas sensor response after filtering, and the sensitivity characteristics of the gas sensor to the pollutant are processed, thereby to determine a gas concentration of the pollutant in the air before filtering. In this way, the concentration measurement is better than a direct measurement with the gas sensor as a result of a low selectivity of the gas sensor.

Figure 1A:
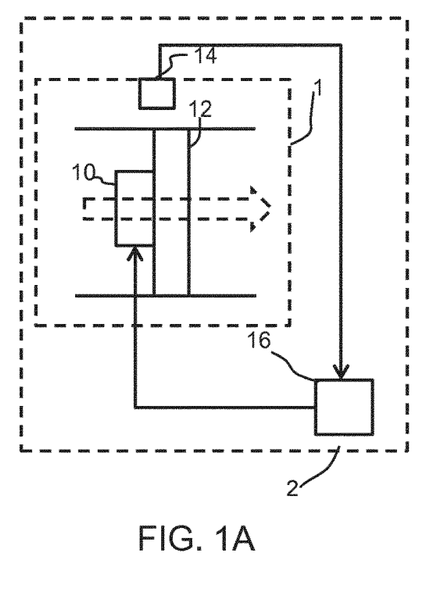
FIGS. 1A and 1B show two examples of an air purifier which includes a sensor system for determining the concentration of a target pollutant.

FIG. 1A shows an example of an air purifier which incorporates a system for measuring a concentration of a pollutant within a gas.

The air purifier 1 is provided within a confined space 2.

An air flow is driven through a sensing and filtering area by a fan 10, although other gas propagation means may be used such as ionic wind or a thermal draft. A filter 12 provides selective filtering of a target pollutant for which the concentration is to be measured. The filter and fan together form the main components of the purifier 1. The target pollutant may itself be a gas, or it may be particulate, or it may be a biological species.

A gas sensor 14 is for sensing a concentration of the pollutant, in particular before the filter, although in practice it will generate a signal in response to other pollutants as well as a result of cross-sensitivity. Thus, it generates a gas sensor response, which is at least partly dependent on the concentration of the target pollutant to be sensed.

Figure 1B:
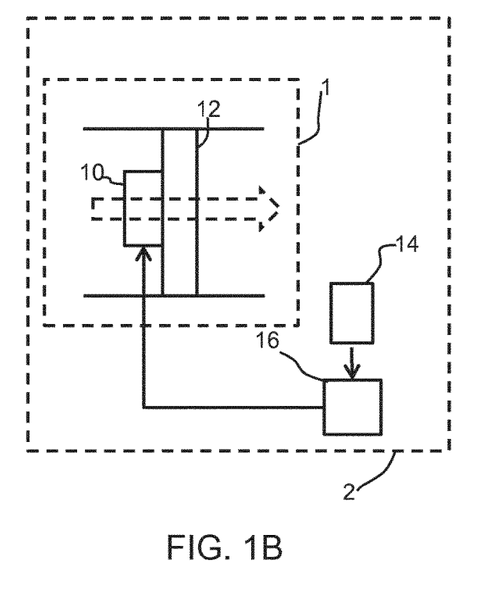

In FIG. 1A the gas sensor 14 is integrated into the air purifier 1. In FIG. 1B, the gas sensor 14 is integrated into an air quality sensor box which is external to the air purifier 1 but within the confined space 2.

The gas sensor is selective to the target pollutant, but it has a selectivity which may be relatively low. For example, the sensor may be exposed to complex mixtures of gas pollutants such as emitted by indoor decoration, or by humans or created during human activities, in which many different pollutants can contribute to the sensor signal because of cross-sensitivity.

Normally, the sensor is calibrated to the target pollutant to correlate the sensor response with target pollutant concentrations. However, when positioned in such a complex mixture of gas pollutants, a too high target pollutant concentration could be calculated due to signal contributions from other species.

In order to overcome this problem, the device contains the filter 12 which removes the target pollutant with a selectivity that fulfills requirements as set out below:

The sensor signal before the filtration step corresponds to $I_{initial}$

The sensor signal after the filtration step corresponds to $I_{final}$

The relationship between the sensor signal and the target pollutant concentration is f(I).

The filter should have such specificity that $f(I_{initial}-I_{final})$, differs less than 50% from the signal as measured with a professional reference sensor system of which the response is not or negligibly influenced by the concentration of other gas pollutants.

More preferably, $f(I_{initial}-I_{final})$ differs less than 25% from the signal as measured with a professional reference sensor system.

Most preferably, $f(I_{initial}-I_{final})$ differs less than 10% from the signal as measured with a professional reference sensor system.

This should apply for general filtering situations, for example down to very low final target levels.

A controller 16 processes a gas sensor response before filtering, a second gas sensor response when the concentration of the pollutant in the air has been reduced by filtering—and the sensitivity characteristics of the gas sensor to the pollutant, thereby to determine a gas concentration of the pollutant in the gas before filtering.

A single gas sensor may be used. It may be used with the fan on or off and it provides a gas sensor reading which is representative of the ambient air at the sensing time. There are two sensor readings, taken at different times, in particular before and after the ambient air has been treated by the filtering of the air purifier. There may also be multiple sensors.

For the example of formaldehyde measurement, Membrapor (trade make) provide sensors with known sensitivity characteristics (i.e. dose response curve) for formaldehyde. An example of a suitable selective filter for formaldehyde is a corrugated filter with TRIS (Tris-hydroxymethyl-aminomethane) as described in WO 97/045189A1 which only filters out Formaldehyde and with high cleaning efficiency and capacity.

The table below shows the selective filter absorption characteristics of the filter.

| gas | absorbable in the filter |
|---|---|
| formaldehyde | yes, at all RH values |
| acetaldehyde | Some |
| propanal | slight at RH > 50% |
| hexanal | no |
| methanol | no |
| ethanol | no |
| iso-propanol | no |
| 1-butanol | no |
| acetone | no |
| acetic acid | yes, at all RH values |
| toluene | no |

The responses of the filter and sensor are preferably orthogonal (other than the target) in the sense that only the target gas is both absorbed by the filter and detected by the sensor. The absorption of acetaldehyde and acetic acid in the example above does not introduce inaccuracy because the gas sensor is not or hardly sensitive to it.

The filter is more selective to the target gas (formaldehyde) and does not remove the pollutants for which the sensor shows a significant cross-sensitivity.

Before the system can be used, the dose response curve of the sensor for the specific gas, in this case formaldehyde, is determined.

Figure 2:
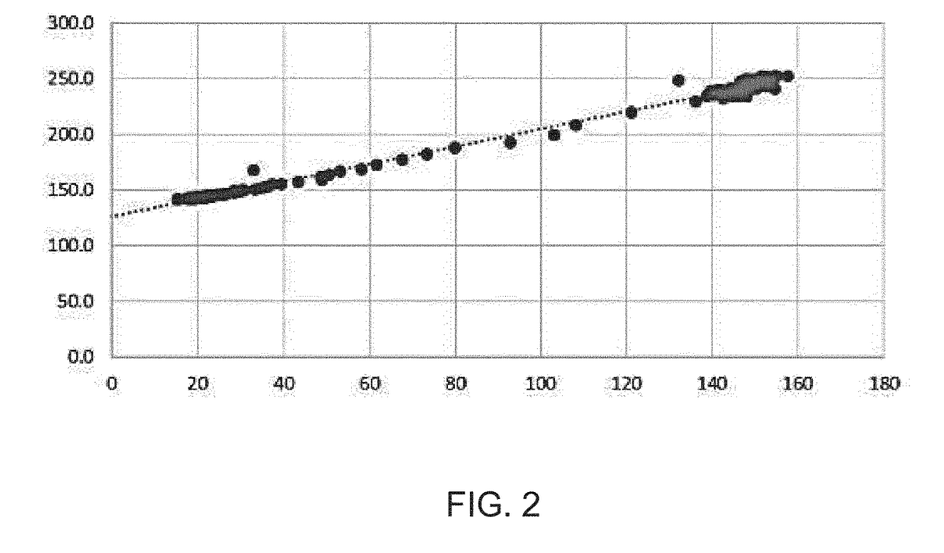
FIG. 2 shows the response of the gas sensor to the concentration of formaldehyde.

FIG. 2 shows along the X-axis the read-out of a professional measurement of formaldehyde, using an Aero-Laser (Trade Mark) formaldehyde analyzer device, which is based on the liquid phase reaction of formaldehyde with acetylacetone (2,4-pentadione) and ammonia, and fluorescence detection of the resultant reaction mixture.

Figure 3:
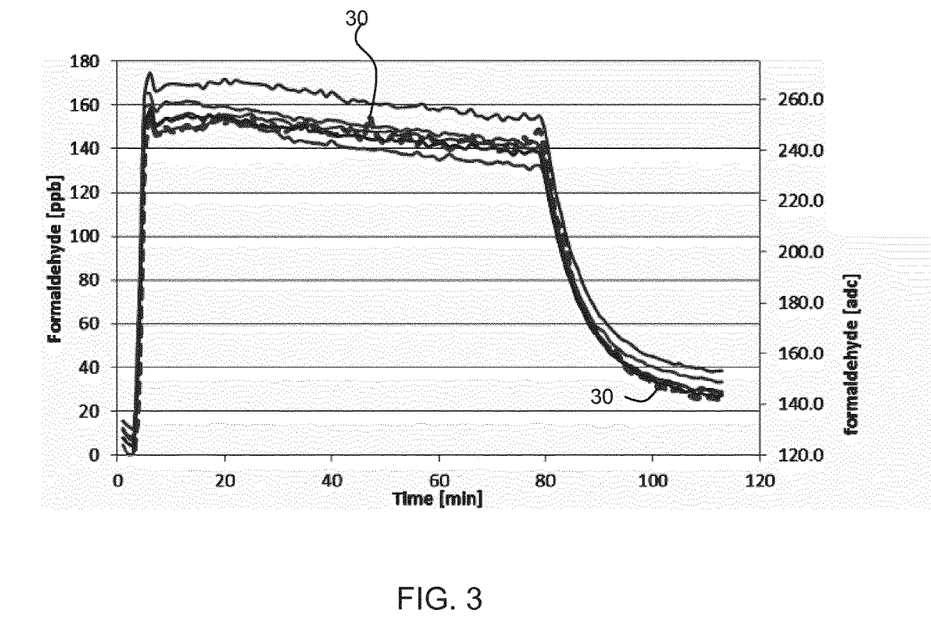
FIG. 3 shows sensor signal readings and a reference instrument reading during a first test procedure and is used to explain how the pollution sensing is carried out.

FIG. 2 shows along the Y-axis the read-out of the Membrapor sensor (as an analog to digital converter output value), during the same controlled increase in formaldehyde concentration as generated by paraformaldehyde evaporation and subsequent removal (see FIG. 3). It shows that the relationship between the Membrapor sensor signal and the actual formaldehyde concentration is almost linear.

In order to determine the target pollutant level accurately, the gas sensor response for the ambient air is measured at two different time points. One measurement is a measurement of a polluted space and the other is a measurement after air purification. As explained above, the air purification is performed done with a filter that removes the target pollutant while not removing the species to which the sensor is cross-sensitive.

The two measurements may be made in either order (i.e. before and after filtering, or after filtering and then once the pollutant levels have returned to their initial values).

In a preferred arrangement, the first sensor response is obtained before air purification. Only after the total air volume in the space being treated (e.g. a room) is purified is the second sensor response obtained.

The first gas sensor response is preferably taken when the pollution level is stable. In this way, it is prevented that rapidly varying influences of human activity on pollutant levels (e.g. cooking) influence the measurement and as a consequence a sensor reading which is representative of the general ambient conditions is obtained. The first gas sensor response may be taken when there are no occupants in the room, for example during the night. The air purifier filtering can be triggered after this stable sensor reading is recorded. Disturbances during the measurement should be prevented as much as possible.

The target pollutant is for example generated by outgassing of decoration rather than by short term peaks created by human activities and for which the sensor is cross-sensitive. For example, by carrying out the measurement during the night, gasses created by human activities are slowly replaced by fresh air from ventilation.

Monitoring takes place during the air purification to determine when the gas sensor response can be obtained. The monitoring for example involves recording the first gas sensor response, and then taking a number of successive measurements to observe the sensor decay. Only when the decay is stable can a final second gas sensor response be processed to enable calculation of the differential value. For the Membrapor sensor, the decaying sensor signal is an indication of increasing air quality. For other sensor types, based on other measurement principles like metal oxide based sensors, the sensor response can instead reach higher values in more purified air due to increase of the sensor resistance.

The sensor decay will not be observed at certain times, for example if a window is open or if some human activity is going on. Human activity in most cases will result in a signal which shows sudden variations of the sensor signal. This will result in unreliable measurements which can therefore be rejected. The difference value will then not be calculated.

The system of the invention does not give an instant measurement but uses post processing to indicate to a user that the air purifier was turned on (for example via an automatic routine with no person present to turn on the device), that the air purifier removed the target pollutant and thus removed the corresponding exposure risk in the room in which there was a problem.

By ensuring a smooth sensor decay before taking a final reading for the pollutant level calculation, inaccurate readings are avoided and a reading is only given when the ambient air reaches a stable and acceptable air quality.

The invention provides a low cost solution in that a single basic sensor design may be used for the successive measurements. The filter is already an existing part of the air purifier.

The sensor may be an integral part of the air purifier as shown in FIG. 1A, or it may be external to it such as part of a separate air quality sensor module as shown in FIG. 1B. The sensor provides a response relating to the target gas at the sensor location. That means that the operation of the air purifier is not determined by the air quality at the air purifier location but by the quality at the sensor location. The sensor can thus be placed at a more consumer relevant position, for example beside the bed or at the office desk where air purifiers are not tolerated. Obviously, the air purifier and the sensor should be positioned in the same confined space.

There may be more than one air purifier in a large room (or office space) and one sensing element. This gives one central air quality read-out reduced cost.

The concentration measurement is for the general gas concentration in a whole space using a single gas sensor (once before air purifying and once after air purifying) rather than measuring the gas concentration in a small gas processing channel. This has an advantage that only one passive gas sensor is needed.

As explained above, the measurement system is used when the composition of the indoor air remains constant during the first measurement (before purification) and during the second measurement (when the target pollutant is removed). Indoor gas compositions vary very rapidly in the event of human activities in the home. However, when people are away from the room or when they are not performing activities (e.g. when sleeping), the gas compositions stabilize, allowing the measurements to be taken.

The measurements may be carried out during the night when in most cases, people will sleep. Alternatively, by analysis of the gas sensor response, a smooth sensor decay is expected during the purification step. If sudden peaks in the sensor signal are observed, the measurement may need further processing or be rejected.

Other sensor signals for sensors in the same space may also be used. If particle levels and/or CO2 levels and/or TVOC sensors are used, and these sensors show indications of human activities during the measurement, the measurement results may again be further processed or be rejected.

The invention may be implemented using low cost MOx (metal oxide) sensors. Electrochemical formaldehyde sensors are far more expensive due to the use of noble metal electrodes and the higher overhead due to smaller production levels. However, MOx sensors show normally extremely high cross-sensitivity to many other VOCs thus making formaldehyde determinations highly inaccurate.

To ensure that the gas sensor responses are suitable and have not been influenced by external factors, the decay or growth behavior of the gas sensor signal is monitored over time, smooth decay changes and stable preceding and subsequent gas sensor readings are indicative of time periods from which suitable gas sensor signals may be taken.

The sensor does not need a generated air flow, and may use natural convection. The air flow used to drive the air flow through the air purifier filter does not need to be directed towards the sensor.

The total cycle time, of measuring the indoor air, operating the air purifier then measuring again the indoor air from which the target pollutant is selectively removed may take from typically 15 minutes to several hours, depending on the air purifier removal effectiveness, its operation mode and the effective room volume. The effective room volume increases if doors are open.

In a preferred implementation, the first gas sensor response is obtained before filtering, and the second gas sensor response is obtained after the filtering, as explained above. However, the two gas sensor responses may be obtained in the opposite order. In this case, the air purifier is turned on to start air purification. The gas sensor is used to measure the indoor air from which the target pollutant is selectively removed. A measurement is obtained when the gas sensor response is stable.

The air purifier is then turned off. When the gas sensor reaches again a stable signal (the signal increases because the removed pollutant is slowly emitted from decoration for example), the sensor may again be used to measure a gas sensor response relating to the original concentration of pollutant. The original concentration of the removed pollutant is again calculated from the difference of the two gas sensor responses.

This process is less preferred as it takes more time and thus there is a larger chance that events occur that intervene with the measurement (for example the inhabitants can wake up, and carry out daily routines which also emit gasses to which the sensor responds).

The operation of the system has been verified by experiment.

The first part of the test was to determine the transfer function of five individual Membrapor formaldehyde sensors (as a calibration step) which are used in known air quality sensor stations.

The five sensors were put in a closed 30 m³ gas test chamber.

A reference instrument was then used to measure accurately the formaldehyde concentration (an Aero-Laser AL4021 device as outlined above).

At time t=0 the test was started with the concentration of formaldehyde below 10 ppb (parts per billion), caused by background concentration and noise.

At t=3 minutes approximately 5 mg of paraformaldehyde was evaporated inside the gas test chamber. The concentration of formaldehyde inside the test chamber then quickly increases to approximately 150 ppb. This concentration then slowly decreases over time to approximately 140 ppb at t=79 minutes.

At t=79 minutes. an air purifier with a selective formaldehyde filter was switched ON and the formaldehyde level decreases in approximately 30 minutes to a level below 30 ppb.

FIG. 3 shows the five gas sensor readings (solid lines) as well as the accurate reading (dotted line, plot 30). The gas sensor readings are measured as analog to digital converter values on the right y-axis scale and the accurate reading is measured as ppb values on the lefty y-axis scale.

The ADC values measured by the five individual sensors were then used to obtain a best fit function to the accurate formaldehyde concentration (ppb) that was measured by the reference instrument.

FIG. 2 is the plot for one such sensor. Plots for the other four sensors are similar. For each sensor, a line of best fit is obtained which then represents the transfer function for each individual sensor. It was found that each such linear transfer function has an $R^2$ regression value of more than 0.99.

A second test was then performed.

In this test, VOC emitting new furniture materials were placed in the 30 m³ test room with the five sensors, the accurate reference instrument and the air purifier. The materials included a rubber mat, laminate floor parts, particle boards, and ceiling boards. The materials emit not only formaldehyde, but also other VOCs to which the formaldehyde sensor may also react (due to cross-sensitivity).

Once the room has been sealed, the VOC level slowly increases until an equilibrium stable level has been reached. This may take several hours.

When the VOC level was stable for at least 2 hours the air purifier was turned on. Almost all the formaldehyde inside the test chamber will then be removed by the air purifier which is allowed to run until a stable low VOC level has been reached.

Figure 4:
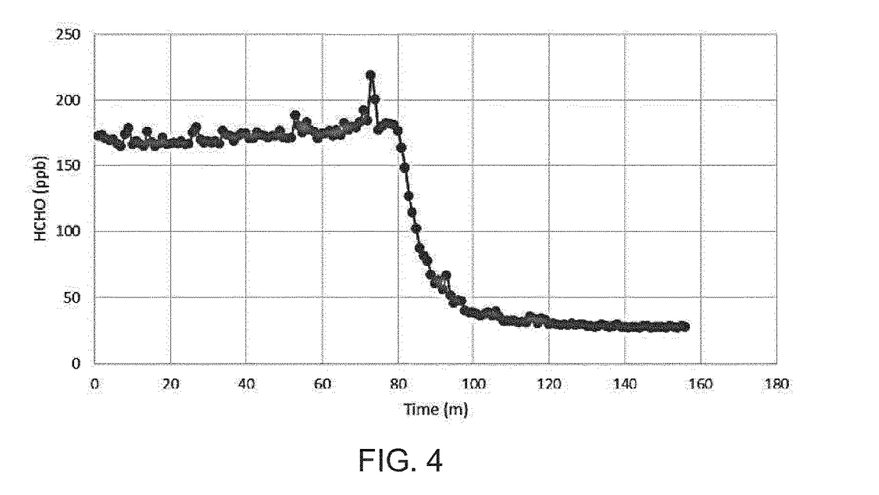
FIG. 4 shows a reference instrument reading during a second test procedure.

FIG. 4 shows the formaldehyde concentration (ppb) measured by the reference instrument as a function of time. The high level corresponds to the stable level that was reached.

The transition from high to low formaldehyde concentration is due to the removal by the air purifier with its dedicated formaldehyde filter. Note that the formaldehyde level does not reach 0 ppb, as there will always be a remaining equilibrium level.

Figure 5:
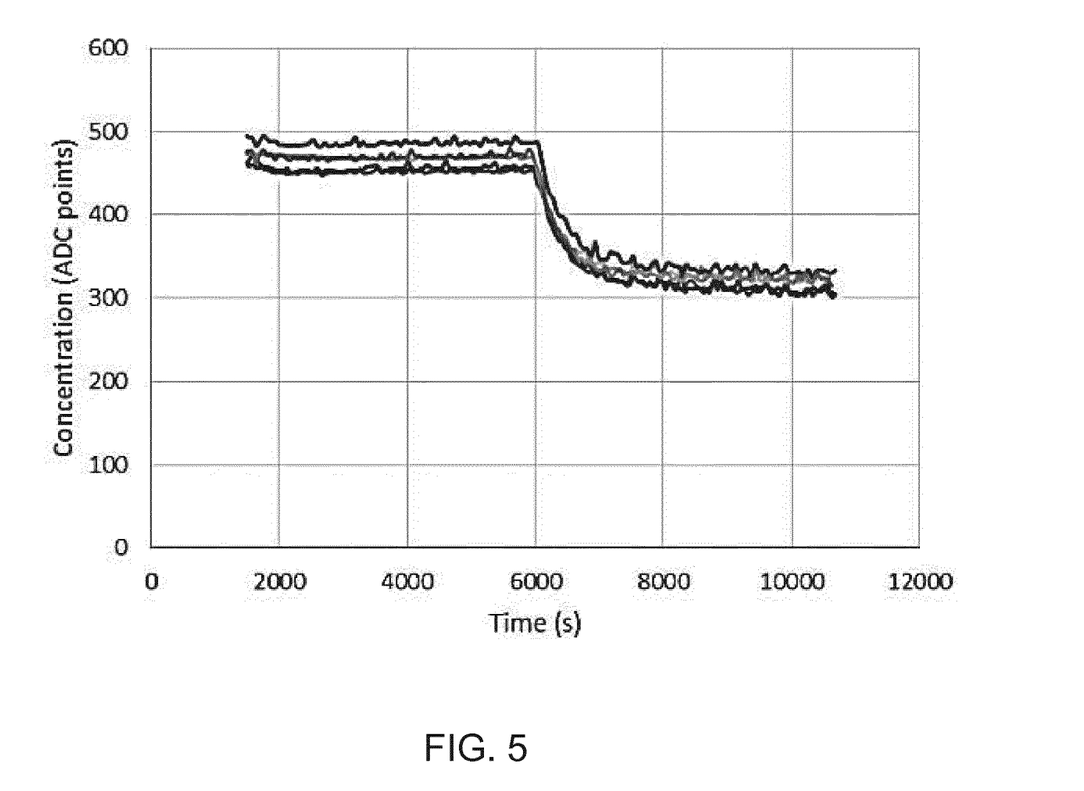
FIG. 5 shows sensor signal readings during the second test procedure.

FIG. 5 shows the VOC levels measured by the five sensors. The values on the y-axis are ADC points and the x-axis is time (in seconds).

FIG. 5 shows that the shape of the five curves matches the shape of the curve of the reference instrument shown in FIG. 4. However, the ADC values will not decrease as much as the reference instrument. At 0 ppb formaldehyde concentration, the formaldehyde sensors will already have an output of approx. 120 to 130 ADC points. This is caused by a hardware offset in the analogue transimpedance amplifier (TIA) circuit. This TIA circuit converts the formaldehyde sensor output current to a voltage that can be interfaced by the microcontroller's analogue to digital converter (ADC).

The table below shows the final result of the measurement.

There is a column for each sensor S1 to S5 and for the reference instrument RI.

| Description | RI | S1 | S2 | S3 | S4 | S5 |
|---|---|---|---|---|---|---|
| AVG value of 4000-5600 second region | 178.3 | 453.0 | 456.5 | 468.8 | 486.7 | 470.3 |
| AVG value of 9.000-10.000 second region | 28.1 | 310.2 | 311.4 | 324.4 | 332.4 | 323.2 |
| Delta in ppb (RI) or ADC points (S1 − S5) | 150.2 | 142.8 | 145.1 | 144.4 | 154.3 | 147.1 |
| ppb with regression function | | 182.2 | 171.7 | 170.6 | 176.2 | 178.6 |
| Relative error | | +21% | +14% | +14% | +17% | +19% |

The average (AVG) ADC value of each sensor S1 to S5 and the reference instrument RI is shown for two time frames. A first, 30 minute time frame (between 4000 and 5600 seconds after start of test) is before formaldehyde removal but with stabilized VOC levels.

A second, 20 minute time frame (between 9000 and 10.000 seconds after start of test) is after formaldehyde removal determined again with the VOC level stabilized.

A difference value is then obtained to give the third row.

The regression function for each individual formaldehyde sensor is then used to convert the result of the subtraction (row 3) into formaldehyde differential concentration values in the fourth row ("ppb with regression function").

The relative error with respect to a differential measurement according to the reference instrument is shown in % in the last row.

The measured (differential) formaldehyde concentrations according using the five sensors correspond well with the differential result of the reference instrument even though the test had other VOCs present.

Figure 6:
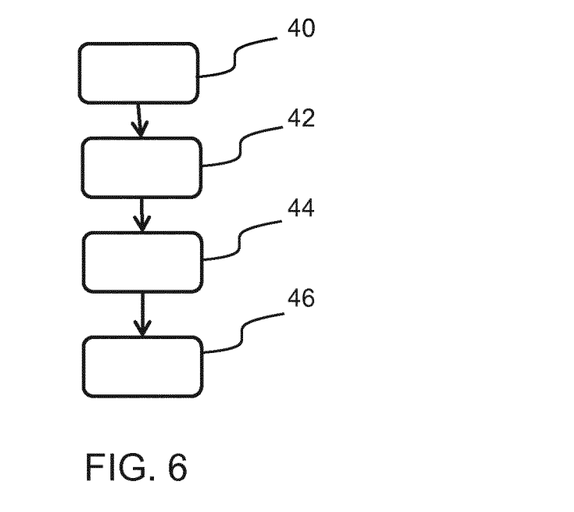
FIG. 6 shows a method of measuring a concentration of a pollutant within a gas.

FIG. 6 shows a method of measuring a concentration of a pollutant within a gas.

In step 40, a gas sensor response is obtained for gas including the pollutant. The measurement is taken when the gas sensor reading is stable, thus indicating the absence of short duration pollution events, and instead representing a general ambient pollutant level. This provides a first gas sensor response.

In step 42, the pollutant is selectively filtered. This filtering is commenced automatically, for example in response to a first pollutant concentration which exceeds a threshold. During this filtering, the concentration is monitored to determine when the filtering is complete. This is when the gas sensor response has stabilized at a new lower level.

In step 44 a gas sensor response is obtained for gas including the pollutant after the filtering, again using the gas sensor. The filtering may then stop because the pollutant has been removed. The concentration will continue to be monitored to detect if and when a further filtering operation is needed.

In step 46, the gas sensor response before filtering, the gas sensor response after filtering, and the sensitivity characteristics of the gas sensor to the pollutant are processed thereby to determine a gas concentration of the pollutant in the gas before filtering. This is based on processing the difference between the gas sensor readings, combined with the known sensitivity function of the sensor. This known function may be provided by the manufacturer, either as general information for that type of sensor or as actual information for the specific sensor as obtained during a calibration process.

The sensor may be integrated into an air purifier or provided as an external component, as mentioned above.

The invention is not limited to formaldehyde sensing. The invention can of course also be used for other combinations of target pollutants, sensors and selective filters The more accurate a sensor response is to a specific pollutant, the more accurate the pollutant concentration that can be given. The background concentration level is not critical as long as the sensor is not saturated. The system can be miniaturized.

The invention is of primary interest in the homes and offices, but it is generally of interest for any space where it is desired to know the concentration of specific target gasses (or particulate matter) unsafe for humans.

The invention is of particular interest for indoor air cleaners, ventilation or HVAC (heating, ventilation and air conditioning systems) and other air handling units.

As discussed above, a controller is used to process the sensor measurements and to control the fan. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application-specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform at the required functions. Various storage media may be fixed within a processor or controller or may be transportable, such that the one or more programs stored thereon can be loaded into a processor or controller. The computer can, in some embodiments, be an external device such as a smart phone. In this case, all data needs to be sent from the sensors/air purifier to such an external device. This may allow to activate the disclosed functionalities once a service (e.g. in the form of an App) is purchased after the purchase of the air purifier.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. Filtering not only refers to removing pollutants from the air stream but can also refer to processes that reduce the target pollutant concentration by reactive processes such as, for example, photocatalytic oxidation and plasma induced processes or it can refer to processes that de-activate biological species such as UV-C irradiation. The mere fact that certain measures are recited in mutually different dependent claims does not indicate that a combination of these measured cannot be used to advantage. Any reference signs in the claims should not be construed as limiting the scope.

The invention claimed is:

1. An air purification system for determining a gas concentration of a pollutant in air before filtering based on at least two distinct samples from the air within a confined space, wherein the at least two samples comprise a first sample being unfiltered air from the confined space and a second sample being filtered air from the confined space, the system comprising:
    a filter for selectively filtering a pollutant from a total air volume in the confined space being treated;
    a gas sensor for sensing a concentration of the pollutant in the air;
    a controller adapted to process a first unfiltered gas sensor response based on analysis of the first unfiltered sample, a second gas sensor response based on analysis of the second filtered sample when the concentration of the pollutant in the total air volume has been reduced by filtering, and the sensitivity characteristics of the gas sensor to the pollutant, thereby to determine the gas concentration of the pollutant in the air before filtering.

2. The system as claimed in claim 1, wherein the filter has greater selectivity of the pollutant than the gas sensor.

3. The system as claimed in claim 1, wherein the pollutant is formaldehyde.

4. The system as claimed in claim 1, wherein the controller is adapted to obtain the first unfiltered pollutant concentration when a stable gas sensor response is obtained.

5. The system as claimed in claim 1, wherein the controller is adapted to operate the filter after a stable gas sensor response is obtained.

6. The system as claimed in claim 1, wherein the controller is adapted to obtain the first unfiltered gas sensor response before the filtering and to obtain the second gas sensor response after the filtering.

7. An air purification method for determining a gas concentration of a target pollutant in air before filtering based on at least two distinct samples from the air in a confined space, wherein the at least two samples comprise a first sample being unfiltered air from the confined space and a second sample being filtered air from the confined space, the method comprising:
    monitoring a gas sensor response using a gas sensor until the gas sensor response has stabilized;
    selectively filtering a target pollutant from a total air volume in the confined space being treated after the gas sensor response has been obtained;
    subsequently obtaining a second gas sensor response after the filtering;
    processing a first unfiltered gas sensor response based on analysis of the first unfiltered sample, the second gas sensor response based on analysis of the second filtered sample when the concentration of the pollutant in the air has been reduced by filtering, and the sensitivity characteristics of the gas sensor to the target pollutant, thereby to determine a concentration of the target pollutant in the air before filtering.

8. The method as claimed in claim 7, comprising obtaining a gas sensor response a plurality of times before selectively filtering and obtaining the first unfiltered gas sensor response when a stable response of the gas sensor is obtained.

9. The method as claimed in claim 7, comprising operating the filter after a stable response of the gas sensor is obtained.

10. The method as claimed in claim 7, comprising obtaining the first unfiltered gas sensor response before the filtering and obtaining the second gas sensor response after the filtering.

11. The method as claimed in claim 7, wherein the filter has greater selectivity of the pollutant than the gas sensor.

12. The method as claimed in claim 7, wherein the pollutant is formaldehyde.

13. The method as claimed in claim 7, comprising obtaining the first unfiltered gas sensor response in a space while there are no occupants.

14. A computer program comprises computer code means which is adapted, when run on a computer, to perform the method of claim 7.

* * * * *